United States Patent [19]
Landfield

[11] Patent Number: 5,939,407
[45] Date of Patent: Aug. 17, 1999

[54] METHOD OF PROTECTING AGAINST NEURON LOSS

[75] Inventor: Philip W. Landfield, Lexington, Ky.

[73] Assignee: University of Kentucky Research Foundation, Lexington, Ky.

[21] Appl. No.: 08/942,560

[22] Filed: Oct. 1, 1997

Related U.S. Application Data

[63] Continuation of application No. 08/594,379, Jan. 30, 1996, abandoned, which is a continuation of application No. 08/091,976, Jul. 15, 1993, abandoned.

[51] Int. Cl.$^6$ .................................................. A01N 45/00
[52] U.S. Cl. ............................................................ 514/167
[58] Field of Search ............................................ 514/167

[56] References Cited

U.S. PATENT DOCUMENTS

| | | | |
|---|---|---|---|
| 4,897,388 | 1/1990 | Malluche ................................. | 514/167 |
| 4,957,909 | 9/1990 | Abou-Gharbia et al. ................. | 514/75 |
| 5,089,517 | 2/1992 | Choi et al. ............................... | 514/411 |
| 5,153,196 | 10/1992 | McQuaid et al. ....................... | 514/250 |
| 5,168,103 | 12/1992 | Kinney et al. ........................... | 514/221 |
| 5,179,109 | 1/1993 | Kamenka et al. ....................... | 514/326 |
| 5,196,421 | 3/1993 | McQuaid et al. ....................... | 514/250 |

FOREIGN PATENT DOCUMENTS 63-104926  5/1988  Japan .

OTHER PUBLICATIONS

Sprott, R.L. (1991) "Development of Animal Models of Aging at the National Institute on Aging" *Neurobiology of Aging* 12(6):635–638.

Flood, D.G. and Coleman, P.D. (1988) "Neuron Numbers and Sizes in Aging Brain: Comparisons of Human, Monkey, and Rodent Data" *Neurobiology of Aging* 9(5/6):453–463.

Kung Sutherland, M. et al. (1992) "Reduction of Vitamin D Hormone Receptor mRNA Levels in Alzheimer As Compared to Huntington Hippocampus: Correlation With Calbindin–28k mRNA Levels" *Molecular Brain Research* 13: 239–250.

Musiol, I.M. et al. (1993) "Vitamin D Nuclear Binding to Neurons of the Alzheimer Pathogenic Region of Nucelus Basalis of Meynert, Central Amygdaloid Group and Nucleus of Diagonal Band of Broca" *Chemical Abstracts* 118(25): Abstract No. 252564.

Musiol, I.M. et al. (1992) "Vitamin D Nuclear Binding to Neurons of the Septal, Substritial and Amygdaloid Area in the Siberian Hamster (*Phodopus Sungorus*) Brain" *Neuroscience* 48(4):841–848.

Saporito, M.S. et al. (1993) "Pharmacological Induction of Nerve Growth Factor mRNA in Adult Rat Brain" *Experimental Neurology* 123(2): 295–302.

Stumpf, W.E. et al. (1982) "Brain Target Sites for 1,25–Dihydroxyvitamin D3" *Science* 215(4538): 1403–1405.

Landfield, P.W. et al. (1992) "Mechanisms of Neuronal Death in Brain Aging and Alzheimer's Disease: Role of Endocrine–Mediated Calcium Dyshomeostasis" *J. Neurobiol.* 23(9):1247–1260.

Landfield, P.W. et al. (1991) "Phosphate/Calcium Aterations in the First Stages of Alzheimer's Disease: Implications for Etiology and Pathogenesis" *J. Neurol. Sci.* 106:221–229.

Ferrier, I.N. et al. (1990) "Reduced Gastrointestinal Absorption of Calcium in Dementia" *Age Ageing* 19:368–375.

Ogihara, T. et al. (1990) "Possible Participation of Calcium–Regulating Factors in Senile Dementia in Elderly Female Subjects" *Gerontology* 36(Supp. 1):25–30.

Kachaturian, Z.S. (1989) "The Role of Calcium Regulation in Brain Aging: Reexamination of a Hypothesis" *Aging* 1:17–34.

Martyn, C.N. et al. (1989) "Calcium Metabolism in Alzheimer's Disease: A Case–Control Study" *Gerontology* 35:153–157.

Gibson, G.E. and Peterson, C. (1987) "Calcium and the Aging Nervous System" *Neurobiol. Aging* 8:329–344.

Orwoll, E.S. and Meier, D.E. (1986) "Alterations In Calcium Vitamin D, and Parathyroid Hormone Physiology In Normal Men With Aging: Relationship to the Development of Senile Osteopenia" *J. Clin. Endocrinol. Metab.* 63:1262–1269.

Kachaturian, Z.S. (1984) "Towards Theories of Brain Aging" *Handbook of Studies on Psychiatry and Old Age* (In: D.S. Kay and G.W. Burrows, eds.) 7–30.

Landfield, P.W. et al. (1981) "Brain Aging Correlates: Retardation by Hormonal Pharmacological Treatments" *Science* 214:581–584.

Landfield, P.W. et al. (1978) "Hippocampal Aging and Adrenocorticoids: Quantitative Correlations" *Science* 202:1098–1102.

Hardman, J.G. and Lumburd, L.E. (1996); "Goodman & Gilman: The Pharmacological Basis of Therapeutics," (9th ed., McGraw Hill, NY) 1529–1536.

Katzman, R. and Saitoh, T (1991); "Advances in Alzheimer's Disease," *The FASB Journal* 5:278–286.

Cohen, G.D.(1983); "Alzheimer's Disease—The Human Concept," *Banbury Report 15; Biological Aspects of Alzheimer's Disease* 3–6.

*Primary Examiner*—Marianne M. Cintins
*Assistant Examiner*—Dwayne C. Jones
*Attorney, Agent, or Firm*—Bromberg & Sunstein LLP

[57] ABSTRACT

The present invention pertains to a method of protecting against neuron loss in a subject by administering a compound that protects against neuron loss by acting through a vitamin D receptor. Some of these compounds may prevent or retard neuron loss by regulating intraneuronal and/or peripheral calcium and phosphate levels. Other compounds of the invention act through a vitamin D receptor to protect against neuron loss through mechanisms not involving calcium or phosphate regulation. A preferred compound is a biologically active form of vitamin D, a precursor, metabolite, or analog of vitamin D. A preferred form of vitamin D is calcitriol. In another embodiment, the compound is a compound that acts by modulating the biological activity of vitamin D, a precursor, metabolite, or analog of vitamin D. For example, the compound may modulate the biological activity of the vitamin D compound by regulating the amount of the vitamin D compound which is available to protect against neuron loss or it may act by altering the ability of the vitamin D compound to protect against neuron loss. In an alternative embodiment, the compound is a compound that protects against neuron loss through a mechanism similar to that of the vitamin D compound but not involving a vitamin D receptor. The compound is administered to a subject in an amount and over a period of time effective to protect against neuron loss.

42 Claims, No Drawings

METHOD OF PROTECTING AGAINST NEURON LOSS

This application is a continuation of copending application Ser. No. 08/594,379 filed on Jan. 30, 1996 which is a continuation of application Ser. No. 08/091,976 filed Jul. 15, 1993 now abandoned.

The work described herein was supported, in part, by grants from the United States government.

BACKGROUND OF THE INVENTION

Unlike many other cell types, neurons cannot be replaced in the adult brain. Thus, neuron loss in the adult brain has crippling and generally irreversible consequences whether it is caused by age, disease, trauma, or combinations thereof.

The cause of neuron loss during aging is unknown. Yet, there is increasing evidence suggesting that almost everyone who lives long enough may succumb to age-related diseases, such as Alzheimer's disease (AD), Parkinson's disease (PD), and stroke, which are generally associated with neuron loss in different regions of the brain. The incidence of many neurodegenerative diseases increases rapidly with aging. For example, the percent of the individuals below age sixty-five who have Alzheimer's disease is less than five percent, but this incidence increases almost exponentially over age sixty-five, and as many as forty-seven percent of individuals over eighty-five years of age may have some form of AD. Katzman, R. and Saitoh, T. (1991) *FASEB J.* 5:278–286; Evans, D. A. et al. (1989) *JAMA* 262:2551–2556. Moreover, the brains of essentially all individuals studied over age eighty contain at least some age- and/or disease-related neuron loss. Matsuyama, H. et al. (1966) *Proceedings of the Fifth International Congress of Neuropathology* (Excerpta Medica International Congress Series No. 100, eds. Luthy, F. et al.) 979–980. Thus, aging itself is the major risk factor for several types of neurodegenerative diseases, indicating that aging increases susceptibility to neuron loss. In fact, there is much evidence that aging, even in the absence of disease, is also associated with neuron loss and memory impairment. Crook, T. et al. (1986) *Devel. Neuropsych.* 2(4):261–276.

Although the cause of neuron loss in aging and neurodegenerative diseases remains unknown, one model has been termed the "altered calcium homeostasis hypothesis". This hypothesis is that dysregulated or elevated intracellular calcium levels is a "final common pathway" for many neurodegenerative conditions and diseases that eventually leads to neuron death. It is based to a large extent on evidence of calcium dysregulation in age-related deterioration of the nervous system in animal models of aging. Khachaturian, Z. S. (1984) *Handbook of Studies on Psychiatry and Old Age* (eds. Kay, D. and Buarrows, G. D., Elsevier, Amsterdam) 7–30; Khachaturian, Z. S. (1989) *Aging* 1:17–34; Gibson, G. E. and Peterson, C. (1987) *Neurobiol. Aging* 8:329–344; Landfield, P. W. (1987) *Neurobiol Aging* 8:346–347. It has also been shown that dysregulated or elevated intracellular calcium can lead to overactivation of enzymes, such as calcium dependent proteases and endonucleases, that can be toxic to cells. Siesjo, B. K. (1981) *J. Cereb. Blood Flow Metab.* 1:155–185; Choi, D. W. (1987) *J Neurosci.* 7:369–379.

While aging appears to affect calcium regulation in the brain, investigations of peripheral calcium regulation in relation to conditions and diseases, for example, AD, a disease marked by extensive neuron loss, notably in the hippocampus, generally have been inconsistent. A number of studies have found that neither parathyroid hormone, vitamin D, nor serum calcium differ systematically between diseased patients and age-matched controls (Shore, D. et al. (1980) *J. Gerontol.* 35:656–662; Singh, S. (1988) *Age Ageing* 17:21–28; Ferrier, I. N. et al. (1990) *Age Ageing* 19:368–375), while a few have found that some aspects of calcium regulation are altered in diseased patients. Martyn, C. N. et al. (1989) *Gerontology* 35:153–157; Ferrier, I. N. et al. (1990) *Age Ageing* 19:368–375; Ogihara, T. et al. (1990) *Gerontology* 36 (Supp. 1): 25–30.

There have also been studies attempting to find alterations in peripheral calcium regulating hormones with normal aging. Some of these studies found changes in calcium regulation and calcium regulating hormones such as vitamin D. Orwoll, E. S. and Meier, D. E. (1986) *J. Clin. Endocrinol. Metab.* 63:1262–1269. However, all of these studies of peripheral calcium regulation in aging and even in AD have been correlational, and none has shown any causal link between peripheral calcium regulating hormones and neuron loss. In fact, none of these studies has even suggested that vitamin D might affect brain calcium regulation or brain neuron loss. This is probably due to the generally held belief that peripheral hormones do not modulate brain calcium regulation. Thus, the concept of calcium regulation by vitamin D has not been related to the altered calcium homeostasis hypothesis of brain aging.

Thus, the genetic or environmental cause(s) of brain aging or death of brain neurons, remain largely undefined. Clearly, whatever the cause, it is the progressive and cumulative effect of neuron death over a long period of time that results in perceptible physiological changes. Progression of cognitive symptoms due to AD have been found in longitudinal studies to be detectable at intervals of no less than one month to one year. Morris, J. C. et al. (1989) *Neurology* 39:1159–1165 (Tables 3 and 6). Hippocampal neuron loss due to normal brain aging is even more gradual. Ball, M. J. (1977) *Acta Neuropathol.* (Berl.) 37:111–118; Coleman, P. D. and Flood, D. G. (1987) *Neurobiol. of Aging* 8:521–545. Thus, testing over a period of not less than one month, up to a period of perhaps several years, is necessary to show evidence of reduced neuron loss upon treatment of a subject with a drug that is purported to be useful in the treatment of age- or disease-related neurodegeneration.

U.S. Pat. No. 4,897,388, issued in 1990 on an application filed in December, 1988 discloses a method of treating patients with Alzheimer's disease through the administration of a safe and effective amount of a biologically active vitamin $D_3$ or $D_2$ material. One patient suffering from Alzheimer's disease was treated with calcitriol for a period of seven days. The patient's condition, the symptoms of which were not defined, reportedly showed improvement. However, the period over which testing was performed is completely insufficient, for the reasons stated above, to show evidence of reduced neuron loss. Additionally, the sample consisting of a single patient is not large enough from which to determine any conclusions, even assuming that the improvement was objectively determined. Finally, there is no explanation of the type of improvement observed but it is likely to be only the relief of AD symptoms caused by peripheral effects of the vitamin D material.

Loss of neurons from the brain is thought to be a general characteristic of aging, affecting virtually all of the population. Progressive neuron loss leads, in many circumstances, to the onset and progression of debilitating neurodegenerative diseases, thus presenting a major healthcare burden for the population. For example, almost $90 billion was spent in 1991 alone on the treatment of patients with Alzheimer's disease. (Alzheimer's Association, Chicago, Ill.) This is just one example of many diseases that may result from neuron loss. Any remedy which could treat, or in the optimal case, prevent, occurrence of age-related neurological diseases by preventing neuron loss would be an immense healthcare savings as well as a great improvement in the health outlook for large number of the population. It is therefore imperative to develop therapies which can halt or slow the progression of neuron loss. Such therapies would optimally work over a long period of time as neuron loss occurs over a long period of time, and be safe in such time frames with efficacious dosages. For the foregoing reasons, there remains a critical need for a method of long term treatment that will prevent or retard neuron loss in a subject.

SUMMARY OF THE INVENTION

The present invention provides a method of protecting a subject against neuron loss by administering to the subject a compound that protects against neuron loss by acting through the vitamin D receptor to prevent or retard neuron loss. The compound is administered in an amount and over a period of time effective to protect against neuron loss. In a preferred embodiment, the period of administration is over a long term, for example, greater than two weeks and preferably one month or longer.

Compounds of the present invention protect against neuron loss by acting through a vitamin D receptor. Some of these compounds may prevent or retard neuron loss by regulating intraneuronal and/or peripheral calcium and phosphate levels. Other compounds of the invention act through a vitamin D receptor to protect against neuron loss through mechanisms not involving calcium or phosphate regulation. A preferred compound is a biologically active form of vitamin D, a precursor, metabolite, or analog of vitamin D (for ease of discussion below, the language "vitamin D compound" and "vitamin D, a precursor, metabolite, or analog of vitamin D" will be used interchangeably) which may or may not regulate calcium and/or phosphate levels. A preferred form of vitamin D is calcitriol.

In another embodiment, the compound that is administered to the subject is a compound that modulates the biological activity of the vitamin D compound. For example, the compound may modulate the biological activity of the vitamin D compound by regulating the amount of endogenous vitamin D compound which is available to protect against neuron loss or it may act by altering the ability of the vitamin D compound to protect against neuron loss. In an alternative embodiment, the compound is a compound that regulates intraneuronal calcium levels through a mechanism similar to that of the vitamin D compounds but not involving a vitamin D receptor (for example, by a post receptor process that modulates intraneuronal calcium levels in a direction similar to that of vitamin D).

BRIEF DESCRIPTION OF THE DRAWINGS

FIGS. 1A, 1B, and 1C represent a schematic depiction of the method used to section the hippocampus in preparation for counting CA1 neurons in rats treated with calcitriol, calcitonin, or a control substance. The elongated hippocampus (FIG. 1A) was dissected free. Blocks of the hippocampus were processed by standard techniques for embedding in plastic. Thin sections (1 μm thick) were cut from the block face (FIG. 1B) and field CA1 neurons were counted in six sections from each animal (FIG. 1C).

FIGS. 2A and 2B are photographs illustrating density of the CA1 neurons in sections of hippocampus of aged rats (26–27 months old). FIG. 2A is a photograph of a representative hippocampal section from field CA1 from an aged control rat. FIG. 2B is a photograph of a representative hippocampal section from field CA1 of an aged rat after 8 months of calcitriol injections.

FIGS. 3A and 3B are bar graphs representing the average number of neurons in the CA1 region of the hippocampus in 100 μm of the CA1 cell layer length for aged male rats injected over an 8 month period (FIG. 3A—age at initiation of treatment was 19–20 months) or a 12 month period (FIG. 3B—age at initiation of treatment was 9–11 months) with either calcitriol, calcitonin, or a control substance.

DETAILED DESCRIPTION OF THE INVENTION

The present invention makes use of the discovery that a subject may be protected against neuron loss by administering to the subject a compound which acts through a vitamin D receptor to prevent and/or retard neuron loss. Because dysregulated calcium levels have been implicated in damage to neural tissues, one mechanism through which some compounds of the present invention may protect against neuron loss is by restoring calcium homeostasis. Other compounds of the present invention act through the vitamin D receptor to protect against neuron loss without regulating calcium levels. Typically, the compound is administered over a long term and in an amount sufficient to protect against neuron loss.

The term "protecting against" is intended to include prevention, retardation, and/or termination of deterioration, impairment, or death of a subject's neurons. The compounds described herein provide protection against neuron loss.

Neuron loss can be the result of any condition of a neuron in which its normal function is compromised. Neuron deterioration can be the result of any condition which compromises neuron function which is likely to lead to neuron loss. Neuron function can be compromised by, for example, altered biochemistry, physiology, or anatomy of a neuron. Deterioration of a neuron may include membrane, dendritic, or synaptic changes which are detrimental to normal neuronal functioning. The cause of the neuron deterioration, impairment, and/or death may be unknown. Alternatively, it may be the result of age- and/or disease-related changes which occur in the nervous system of a subject.

When neuron loss is described herein as "age-related", it is intended to include neuron loss resulting from known and unknown bodily changes of a subject which are associated with aging. When neuron loss is described herein as "disease-related", it is intended to include neuron loss resulting from known and unknown bodily changes of a subject which are associated with disease. It should be understood, however, that these terms are not mutually exclusive and that, in fact, many conditions that result in the loss of neurons are both age- and disease-related.

Some of the more common age-related diseases associated with neuron loss and changes in neuronal morphology include, for example, Alzheimer's disease, Pick's disease, Parkinson's disease, vascular disease, Huntington's disease, and Age-Associated Memory Impairment. In Alzheimer's patients, neuron loss is most notable in the hippocampus, frontal, parietal, and anterior temporal cortices, amygdala, and the olfactory system. The most prominently affected zones of the hippocampus include the CA1 region, the subiculum, and the entorhinal cortex. Memory loss is considered the earliest and most representative cognitive change because the hippocampus is well known to play a crucial role in memory. Pick's disease is characterized by severe neuronal degeneration in the neocortex of the frontal and anterior temporal lobes which is sometimes accompanied by death of neurons in the striatum. Parkinson's disease can be identified by the loss of neurons in the substantia nigra and the locus ceruleus. Huntington's disease is characterized by degeneration of the intrastriatal and cortical cholinergic neurons and GABA-ergic neurons. Parkinson's and Huntington's diseases are usually associated with movement disorders, but often show cognitive impairment (memory loss) as well.

Age-Associated Memory Impairment (AAMI) is another age-associated disorder that is characterized by memory loss in healthy, elderly individuals in the later decades of life. Crook, T. et al. (1986) *Devel. Neuropsych.* 2(4):261–276. Presently, the neural basis for AAMI has not been precisely defined. However, neuron death with aging has been reported to occur in many species in brain regions implicated in memory, including cortex, hippocampus, amygdala, basal ganglia, cholinergic basal forebrain, locus ceruleus, raphe nuclei, and cerebellum. Crook, T. et al. (1986) *Devel. Neuropsych.* 2(4):261–276.

Subjects who can be treated by the method of this invention include living organisms, e.g. mammals, susceptible to age- and/or disease-related neuron loss. Examples of subjects include humans, dogs, cats, rats, and mice. Lower mammal models using, for example, rats or mice can be used to predict modes of general brain aging and associated neuron loss in higher mammals, such as humans.

Aging rodent brains do not develop senile plaques and neurofibrillary tangles. Most recent studies suggest, however, that loss or shrinkage of neurons, dendrites, and/or synapses is more closely correlated with either dementia or aging than are plaques and tangles. Terry, R. D. et al. (1987) *Ann. Neurol.* 21:530–539; Terry, R. D. et al. (1990) *J. Neuropathol. Exp. Neurol.* 49:335; Buell, S. J. and Coleman, P. D. (1981) *Brain Res.* 214:23–41; Scheff, S. W. et al. (1990) *Neurobiol. Aging* 11:29–37. Aging rats exhibit neuronal cell loss in the pyramidal cells of the hippocampus, especially in field CA1, (Landfield, P. W. et al. (1981) *Science* 214:581–584; Landfield, P. W. (1987) *Prog. Brain Res.* 72:279–300; Kerr, D. S. et al. (1991) *J. Neurosci.* 11:1316–1324) as well as cell loss or dendritic/synaptic changes in some other brain regions. Coleman, P. D. and Flood, D. G. (1987) *Neurobiol. Aging* 8:521–545; Geinisman, Y. et al. (1986) *Brain Res.* 398:266–275. Moreover, aging rodents show extensive hippocampal astrocyte hypertrophy (Landfield, P. W. et al. (1977) *J. Gerontol.* 32:3–12; Landfield, P. W. et al. (1978) *Science* 202:1098–1102; Geinisman, Y. et al. (1978) *Am. J. Anat.* 153:537–544) just as do aging humans. Wisniewski, H. M. and Terry, R. D. (1973) *Progress in Brain Research* (ed. Ford, D. M. Elsevier, Amsterdam) 40:167–186; Hansen, L. A. et al. (1987) *Neurobiol. Aging* 8:1–6. In addition, loss of neurons in field CA1 of the hippocampus is a consistent correlate of aging across species, and is also prominent in human neurodegenerative diseases, such as AD. For these reasons, the study of neuron loss in aging rats, for example, is predictive of general mechanisms of brain aging and associated neuron loss in humans.

Because of the great difficulty associated with measuring brain neuron loss in living humans or even in autopsy material, which is highly variable and often shows massive changes due to the postmortem interval prior to fixation, many neuroprotective inventions have been based on in vitro tissue culture systems of neurons from embryonic rodent pups (See e.g. U.S. Pat. No. 5,179,109-fetal rat tissue culture), or other mammalian (See e.g. U.S. Pat. No. 5,089,517-fetal mouse tissue culture) or non-mammalian animal models. These inventions have been for protection of peripheral as well as central nervous system neurons in animal or tissue culture models of ischemia, stroke, trauma, nerve crush, AD, and PD, etc. Neuron deterioration in these model systems is often proved by experimental trauma or intervention (e.g. application of toxins, nerve crush, interruption of oxygen supply, etc.). For example, in order to demonstrate that certain N-methyl-D-aspartate (NMDA), an excitatory amino acid neurotransmitter receptor, antagonists were useful as anticonvulsants and neuroprotectants, the inventors in U.S. Pat. No. 4,957,909 employed a model wherein Swiss-albino mice and rat hippocampal neurons were subjected to overstimulation of excitatory amino acid receptors subsequent to treatment with the NMDA antagonists. A similar study was performed wherein the utility of certain NMDA antagonists as agents that prevent neurodegeneration was demonstrated by treating mice with NMDA subsequent to treatment with the NMDA antagonists. U.S. Pat. No. 5,168,103. Another experimental model wherein the inventors, in order to demonstrate the ability of indolactam V compounds to prevent destruction of neocortical neurons, exposed in vitro cultures of fetal mouse neurons and glial cells to various glutamate agonists, such as kainate, NMDA, and α-amino-3-hydroxy-5-methyl-4-isoxazolepronate (AMPA). U.S. Pat. No. 5,089,517. See also U.S. Pat. No. 5,170,109 (treatment of rat cortical/hippocampal neuron cultures with glutamate prior to treatment with neuroprotective compound); U.S. Pat. Nos. 5,163,196 and 5,196,421 (neuroprotective excitatory amino acid receptor antagonists inhibit glycine, kainate, AMPA receptor binding in rats).

However, the present animal model represents an improvement in the model for age-associated neuroprotection because it relates to an intact animal, which is generally preferred over tissue culture models, and employs a strain of rat that was developed by the National Institute on Aging as a premier model of mammalian aging. The particular rat strain (Brown Norway/Fischer 344 F1 cross rats) was selected as such a model due to its normal pattern of aging, with few indications of abnormal pathology. This strain also loses neurons in field CA1 of the hippocampus with aging and exhibits memory loss. This system represents one of the most natural animal models of neuron degeneration and/or deterioration because it reflects a gradual loss of neurons. Furthermore, the neuron loss is not provoked by experimental intervention or abnormal pathology. Its brain aging pattern is also highly analogous to human and other mammalian species' brain aging patterns.

The compound is administered through a route which allows the compound to perform its intended function of protecting against neuron loss in a subject. Examples of routes of administration which may be used in this method include parenteral (subcutaneous, intravenous, intramuscular, intraarterial, intraperitoneal, intrathecal, intracardiac, and intrasternal), enteral administration (i.e. administration via the digestive tract), mucosal administration, and percutaneous administration. Depending on the route of administration, the compound may be coated with or in a material to protect it from the natural conditions which may detrimentally affect its ability to perform its intended function. A particularly convenient method of administering a compound of the present invention, for example a vitamin D compound, is percutaneous administration.

The administration of the compound is performed in accordance with the invention, at dosages and for periods of time effective to protect against the loss of neurons in a subject. Dosage regimes may be adjusted for purposes of improving the therapeutic response to the compound. For example, several divided doses may be administered daily or the dose may be proportionally reduced as indicated by the exigencies of the therapeutic situation.

Compounds of the present invention protect against neuron loss by acting through a vitamin D receptor. Vitamin D receptors are well known to exist in the periphery but have also been found in the brain, particularly in the hippocampus and neocortex. Some of these compounds may prevent or retard neuron loss by regulating intraneuronal and/or peripheral calcium and phosphate levels. Other compounds of the invention act through a vitamin D receptor to protect against neuron loss through mechanisms not involving calcium or phosphate regulation. The compounds that act by regulating calcium and/or phosphate levels modulate calcium and/or phosphate homeostasis of either peripheral or intraneuronal calcium and/or phosphate or restore dysregulated calcium to normal levels, thereby providing protection against neuron loss.

One way a compound can protect against neuron loss by acting through the vitamin D receptor is by modulating the biological activity of a vitamin D compound. This can be done by modulating the amount of the vitamin D compound that is available to protect against neuron loss. Generally, the compound will increase the amount of vitamin D compound that is available to protect against neuron loss by increasing the synthesis or expression of the vitamin D compound. For example, the biphosphonate YM175 (methylene-1,1-biphosphonate) has been found to stimulate renal production of 1,25 dihydroxy-vitamin D by stimulating renal 1-hydroxylase activity in rats. Nagao, Y. et al. (November 1991) *Biochem. Biophys. Res. Comm.* 180(3): 1172–1178. Renal 1-hydroxylase is an enzyme that hydroxylates 25 dihydroxy vitamin D to yield 1,25 dihydroxy vitamin D, or calcitriol which is believed to be one of the most active metabolites of vitamin D. Another biphosphonate, HPeBP (1-hydroxypentane-1,1-biphosphonate), has been shown to induce stimulation of 1,25 dihydroxy-vitamin D. Bonjour, J.-P. et al. (1988) *Am. J. Physiol.* 254:E260–E264. Vitamin D receptor agonists also contribute to the regulation of the amount of the vitamin D compound that is available to protect against neuron loss.

Another way in which a compound of the present invention can protect against neuron loss by acting through a vitamin D receptor is by altering the ability of the vitamin D compound to protect against neuron loss. Such compounds include binding proteins, such as vitamin D-binding protein. These proteins may act by increasing the stability of the vitamin D compound. There are still other neuroprotective compounds, such as other steroids or related compounds, which may not act through the vitamin D receptor but may regulate, directly or indirectly, calcium and/or phosphate levels in a manner similar to that of vitamin D (for example, by a post receptor process that modulates intraneuronal calcium levels in a direction similar to that of vitamin D). Such compounds include, for example, glucocorticoid receptor antagonists such as mifepristone, mifepristone derivatives (See e.g. U.S. Pat. No. 4,386,085), and dehydroepiandrosterone (DHEA).

In a preferred embodiment, the compound is a biologically active form of vitamin D, or a precursor, metabolite, or analog of vitamin D. Vitamin D is generally classified as a steroid hormone because of its hormonelike relationship with calcium and phosphate metabolism, its pathway of molecular modification to yield active metabolites, and its mechanism of action which is similar to those of other steroid hormones. The language "vitamin D, precursor, metabolite, or analog of vitamin D" is intended to include vitamin D or an analog thereof, in any stage of its metabolism. This language is also intended to include mixtures of different metabolic forms of vitamin D or a vitamin D analog. The vitamin D compounds may preserve or restore calcium homeostasis by interfering with mechanisms which result in neurotoxic levels of calcium and/or phosphate. Alternatively, the vitamin D compounds may protect against neuron loss through mechanisms not involving calcium regulation. Generally, there are two sources of vitamin D in most mammals. One source is vitamin D produced in the skin by ultraviolet irradiation ($D_3$ or cholecalciferol). Another source is vitamin D ingested in the diet ($D_2$ or ergocalciferol). $D_2$ and $D_3$ have identical biological actions. Vitamin $D_2$ and $D_3$ compounds include, for example, dihydrotachysterol$_2$, dihydrotachysterol$_3$, 5,6-trans cholecalciferol, 25-hydroxy-5,6-trans cholecalciferol, 1α-hydroxy ergocalciferol (1α-OHD$_2$), 25-hydroxy ergocalciferol (25-OHD$_2$), 1α, 25-dihydroxy ergocalciferol (1α, 25-(OH)$_2$D$_2$), 1α, 25-dihydroxy cholecalciferol (1α, 25-(OH)$_2$D$_3$), 1α, 24, 25-trihydroxy cholecalciferol (1α, 24, 25-(OH)$_3$D$_3$), 24,25-dihydroxy cholecalciferol (24,25-(OH)$_2$D$_3$), 1α, 24-dihydroxy-25-fluoro cholecalciferol (1α, 24-(OH)$_2$ 25-FD$_3$), 25-hydroxy cholecalciferol (25-OHD$_3$), and 1α-hydroxy cholecalciferol (1α-OHD$_3$).

Vitamin $D_2$ and $D_3$ precursors and metabolites are also biologically active. Vitamin $D_2$ or $D_3$ precursors and metabolites include, for example, 1α25-dihydroxy-B 7-dehydrocholesterol (1α, 25-(OH)$_2$ proD$_3$), 1α, 24,25-trihydroxy-7-dehydrocholesterol (1α, 24,25-(OH)$_3$ proD$_3$), 24,25-dihydroxy-7-dehydrocholesterol (24,25-(OH)$_2$-proD3), 1α-hydroxy-7-dehydrocholesterol (1α-OH proD$_3$), 1α, 24-dihydroxy-25-fluoro-7-dehydrocholesterol (1α, 24-(OH)$_2$-25F proD3), 25,26-dihydroxy-7-dehydrocholesterol (25 ,26-(OH)$_2$ proD$_3$), 25-hydroxy-7-dehydrocholesterol (25-OH proD$_3$), 25-hydroxy ergosterol (25-OH proD$_2$), 1α, 25-dihydroxy ergosterol (1α, 25-(OH)$_2$ proD$_2$), 1α, 25-dihydroxy precholecalciferol (1α, 25-(OH)$_2$ preD$_3$), 1α, 24,25-trihydroxy precholecalciferol (1α, 24, 25-(OH)$_3$ preD3), 24,25-dihydroxy precholecalciferol (24,25-(OH)$_2$-preD$_3$), 1α-hydroxy precholecalciferol (1α-OH preD$_3$), 1α, 24-dihydroxy-25-fluoro-precholecalciferol (1α, 24-(OH)$_2$-25F preD$_3$), 25-hydroxy-precholecalciferol (25-OH preD$_3$), 1α-hydroxy-previtamin $D_2$ (1α-OH preD$_2$), 25-hydroxy-previtamin $D_2$ (25-OH preD$_2$), and 1α, 25-dihydroxy-previtamin $D_2$ (1α, 25-(OH)$_2$ preD$_2$).

A vitamin $D_3$ metabolite which is particularly useful in the method of the present invention is 1,25 dihydroxycholecalciferol (1,25 (OH)$_2$-D$_3$ or calcitriol). Calcitriol is believed to be one of the most active forms of vitamin $D_3$. It is presently commercially available in capsule form (ROCALTROL®, Roche Laboratories) or in injection form (CALCIJEX®, Abbott Laboratories, Inc.).

The term "biologically active" is intended to include an activity for the vitamin D, precursor, metabolite, or analog of vitamin D, which allows it to perform its intended function. It is known in the art that vitamin D compounds display varying degrees of activity and it is contemplated that any of the biologically active forms of vitamin D can be used in the method of this invention.

The compound is administered over a period of time effective to protect against neuron loss in a subject. Typically, the treatment period will be over a long term. The phrase "long term," as used herein is a time period of such a duration that a subject treated with the compound, when compared with a subject not so treated, is protected against neuron loss. Generally, changes in neuron number are not apparent until at least approximately two weeks into the treatment. Thus, "long term" administration of the compound refers to a period of administration of greater than two weeks, and usually about one month, or longer. Preferably, the administration is over a period of time from about six months to one year or longer.

An amount of the compound which is effective to protect against neuron loss in a subject is the amount of compound sufficient to prevent, retard, and/or terminate deterioration, impairment, and/or death of a neuron. The dose of the compound sufficient to protect against neuron loss is dependent both on the specific activity of the compound and its concentration. Choice of an appropriate dose can be determined on an individual basis and will be based, at least in part, on consideration of the severity of the symptoms to be treated and the activity of the specific compound used. Further, the effective amounts of the compound may vary according to the age, sex, and weight of the subject being treated. Thus, an effective amount of the compound can be determined by one of ordinary skill in the art employing such factors as described above using no more than routine experimentation.

The invention is further illustrated by the following non-limiting examples. The contents of all references and issued patents cited throughout this application are expressly incorporated herein by reference.

EXAMPLES

Animals

The rats used in this experiment were male Brown Norway x Fischer 344 F1 cross hybrid rats which were obtained from the National Center for Toxicology Research (Jefferson, Ark.). These F1 cross hybrid rats were maintained in a largely germ-free (specific pathogen free) environment and have a mean longevity when maintained in such a controlled environment of about 29–30 months of age. The animals continued to be maintained, throughout the injection period, in laminar air flow filter barriers in animal facilities and fed, ad libitum, a diet of rodent chow and water. Animals were weighed weekly to monitor any effect of the drugs on their body weight and health. Food and water study was done during the first months to monitor effect of drugs on their food consumption. All animals that displayed any physical health problems were necropsied and blood was taken for analysis. During necropsy, organ condition and pathologies were noted.

Animals were kept on six foot animal racks and each drug group had the same number of animals in every position at the start of the study. Positioning the rats in order to equalize the amount of light to which they were exposed was important because serum vitamin D levels can be influenced by the amount of light that the rats received.

Three groups, each consisting of between eight and thirteen rats, were carefully selected and matched for age and body weight at the start of each study. In the first study, rats between 18 and 19 months of age were subjected to drug injections for a period of 8 months. At the end of the injection period, the rats were between 26 and 27 months old. In the second study, rats between 9 to 11 months of age were subjected to drug injections for a period of 12 months. At the end of the injection period, the rats were between 21 and 23 months old.

Drugs

Calcitriol (CALCIJEX®, in 2 mg/ml vials, was obtained from Abbott Laboratories, Inc (Abbott Park, Ill.). A test group of rats received subcutaneous injections of calcitriol daily at the rate of 20 ng/rat/day for five consecutive days per week. For the 18–19 month old rats, the injections continued for a period of 8 months. For the 9–11 month old rats, the injections continued for a period of 12 months.

Salmon calcitonin was obtained from either Bachem (Torrance, Calif.) or Calbiochem (San Diego, Calif.) in 1 mg vials. The peptide was kept in aliquot form in light-free conditions in a $-40°$ C. freezer and diluted daily for injection. The diluant consisted of a filtered and autoclaved solution of the following components: 20 mg polysorbate, 45 mg NaCl, 300 mg ascorbic acid, 228 mg dibasic phosphate buffer, 54 mg monophosphate buffer, and 30 mg EDTA. This diluant was used in order to match the vehicle in which calcitriol is commercially available. A second group of rats received subcutaneous injections at a dose of 2 IU/rat/day (five days/week) of calcitonin. A control group of rats received subcutaneous injections of a control solution consisting of the same ingredients in the same amounts as the CALCIJEX® solutions, minus the calcitriol or calcitonin, at the same rate. For the 18–19 month old rats, the injections of calcitonin and the control substance continued for a period of 8 months. For the 9–11 month old rats, the injections of calcitonin and the control substance continued for a period of 12 months.

In order to assure that the drugs were biologically active and to determine that there were no toxic side effects produced by the drugs, the animals that were used for hippocampal cell density measurements in the 8 month injection study also had blood analysis tests done. (Table I) Blood was collected after the injection of sodium pentobarbital and just prior to intracardial perfusion, using a vacutainer, for blood collection.

Tissue Preparation

Upon completion of both the 8 and 12 month injection periods, the animals in the calcitriol-treated, calcitonin-treated and control-treated groups were injected with a lethal dose of sodium pentobarbital. The animals were allowed to reach a deep level of anesthesia before the perfusion was initiated. Blood was taken from the left ventricle just prior to the perfusion by the fixative. Table I illustrates the effects of calcitriol and calcitonin on the levels of calcium in the blood of the rats which were 18–19 months old at the initiation of the injections after 8 months of injections. As was expected, calcitriol treatment resulted in a significantly increased level of blood calcium and phosphorous over that in the blood of controls. Calcitonin treatment resulted in blood calcium levels slightly but not significantly above that found in the blood of controls. Data shown are means±S.E.M.

TABLE I

BLOOD SUMMARY FOR BROWN NORWAY X F344
RATS AFTER 8 MONTHS OF INJECTION

|  | Control | Calcitriol | Calcitonin |
|---|---|---|---|
| Body Weight | 574.4 ± | 529.2 ± | 559.7 ± |
| (p = 0.2171) | 26.9 | 13.11 | 14.93 |
| Sodium | 144.6 ± | 146.2 ± | 146.4 ± |
| (p = 0.2831) | 1.32 | 0.48 | 0.62 |
| Potassium | 5.15 ± | 5.46 ± | 5.13 ± |
| (p = 0.5890) | .328 | 0.272 | 0.195 |
| Chloride | 100.73 ± | 98.42 ± | 93.60 ± |
| (p = 0.5403) | 1.01 | 0.489 | 6.966 |
| CO2 | 29.00 ± | 29.75 ± | 29.66 ± |
| (p = 0.7400) | 0.735 | 0.657 | 0.744 |
| Urea | 19.91 ± | 15.92 ± | 18.86 ± |

TABLE I-continued

BLOOD SUMMARY FOR BROWN NORWAY X F344
RATS AFTER 8 MONTHS OF INJECTION

|  | Control | Calcitriol | Calcitonin |
|---|---|---|---|
| (p = 0.3365) | 1.237 | 0.983 | 2.595 |
| Glucose | 168.82 ± | 183.75 ± | 166.20 ± |
| (p = 0.4467) | 14.100 | 8.776 | 9.643 |
| Calcium | 10.282 ± | 11.10** ± | 10.314 ± |
| (p = 0.0003)** | .13772 | .13236 | .16127 |
| Phosphorus | 4.336 ± | 4.842** ± | 4.100 ± |
| (p = 0.0065)** | .15954 | 0.1727 | 0.1607 |
| Creatinine | 0.555 ± | 0.4667 ± | 0.5933 ± |
| (p = 0.0963) | 0.0389 | 0.02346 | 0.0529 |
| Uric Acid | 0.6545 ± | 0.9833 ± | 0.9600 ± |
| (p = 0.5229) | 0.2471 | 0.2219 | 0.2077 |
| Cholesterol | 101.727 ± | 90.250 ± | 89.733 ± |
| (p = 0.1464) | 5.0737 | 4.814 | 4.516 |
| Protein | 6.100 ± | 6.2250 ± | 6.0467 ± |
| (p = 0.6626) | 0.1697 | 0.0814 | 0.1653 |
| Albumin | 2.918 ± | 3.0500 ± | 2.8733 ± |
| (p = 0.5839) | 0.1902 | 0.302 | 0.127 |
| Total Bilirubin | 0.200 ± | 0.208 ± | 0.213 ± |
| (p = 0.9095) | 0.245 | 0.0239 | 0.0199 |
| Alkaline | 127.636 ± | 99.00 ± | 87.333 ± |
| (p = 0.1386) | 27.47 | 5.5402 | 6.9324 |
| Glut. Oxaloacetic Transaminase | 116.091 ± | 103.167 ± | 110.987 ± |
| (p = 0.8486) | 15.653 | 17.779 | 14.398 |
| Lactate Dehydrogenase | 277.818 ± | 284.00 ± | 377.600 ± |
| (p = 0.5820) | 74.7116 | 70.393 | 87.925 |
| Iron | 171.546 ± | 195.083 ± | 187.533 ± |
| (p = 0.766) | 26.899 | 13.266 | 24.778 |
| Magnesium | 1.813 ± | 1.725 ± | 1.7091 ± |
| (p = 0.4625) | 0.0426 | 0.0670 | 0.0574 |
| Corticosterone | 302.143 ± | 280.273 ± | 283.364 ± |
| (p = NS) | 55.019 | 32.364 | 48.163 |

Subsequently, the animals were perfused with a 2% glutaraldehyde-2% paraformaldehyde fixative solution at 4° C. for 30 minutes. After perfusion was completed, the brain of each animal was dissected and placed in the 2% glutaraldehyde-2% paraformaldehyde fixative overnight at 4° C.

The frontal lobes and cerebellum were dissected away and the remaining hippocampus and cortex were cut in 250 $\mu$m thick sections starting at the most anterior portion of the hippocampus. The resulting sections were collected serially into sodium cacodylate buffer. The section that was 2250 $\mu$m posterior in the first experiment and 1750 $\mu$m posterior in the second experiment was consistently used for comparison among the three groups of animals.

Light Microscopy

The 250 $\mu$m-thick sections were processed as indicated by the standard embedding for electron microscopy or for "semithin" sections used in light microscopy. Peters, A. and Palay, S. L., The Fine Structure of the Nervous System (Harper & Row, New York 1970); Landfield, P. W. et al. (1981) Neurobiol. Aging 2:265–275. Blocks were infiltrated with Epon 812 from Ted Pella (Redding, Calif.).

After embedding, 1 $\mu$m-thick semithin sections containing at least several hundred $\mu$m of the CA1 neuron layer were cut from the face of the 250 $\mu$m-thick section. (See FIGS. 1A, 1B, and 1C) The first five wells of a glass slide were filled with adjacent semithin sections and then the next 50 $\mu$m of the section block was discarded. Then five additional semithin sections were cut serially into another five wells. Discarding the intervening 50 $\mu$m allowed for sampling of a larger region of the hippocampus. Semithin sections were then stained with Toluidine Blue and coverslipped for analysis.

For each animal, three pairs of the adjacent sections were photographed. The cells that had the beginning "top" of one neuron starting in one photograph but not in the other adjacent section of the pair were counted for each animal. This is a new stereological method that provides a reliable index of number of neurons in a section, which is unbiased by shape or size of the neurons. Pakkenberg, B. and Gundersen, H. J. G. (1989) APMIS 97:677–681; West, M. and Gunderson, H. (1990) J. Comp. Neurol. 296:1–22. The length of the cell layer in each section was measured using a calibrated imaging system (Sigma Scan) and the average number of CA1 neurons/100 $\mu$m of the CA1 cell layer length was obtained. FIGS. 2A and 2B show photographs illustrating CA1 neurons in the hippocampus of rats between the ages of 26–27 months after they have been injected over an 8 month period with a control substance (FIG. 2A) or calcitriol (FIG. 2B). After the injection period, the hippocampal tissue was embedded, sectioned (1 $\mu$m), and stained with Toluidine Blue. After calcitriol treatment (FIG. 2B), a greater density of neurons appears in the hippocampal section. After treatment with the control substance (FIG. 2A), there are gaps and empty regions where the hippocampal neurons have died.

The average number of CA1 neurons/100 $\mu$m of the CA1 cell layer length for the calcitriol, calcitonin, and control groups for both experiments is shown in FIGS. 3A and 3B. FIGS. 3A and 3B show bar graphs illustrating the number of CA1 neurons/100 $\mu$m of the CA1 cell layer length in hippocampal sections of calcitriol-treated, calcitonin-treated, and control-treated rats after 8 and 12 months of injections. Rats of two different age groups were used, the group treated for 8 months being substantially older (18–19 months) than the group treated for one year (9–11 months) at the start of the study. Neuron loss in the rats that were treated with calcitriol was prevented, inhibited, and/or retarded as compared to the rats treated with the control injection. The average number of CA1 neurons/100 $\mu$m of the CA1 cell layer length in the hippocampal sections of the 12 month (FIG. 3A) calcitriol-treated group was about 1.65, while the average number of CA1 neurons/100 $\mu$m in the control group was about 1.4. The calcitonin-treated group of rats had the lowest average number of CA1 neurons/100 $\mu$m with about 1.3 CA1 neurons/100 $\mu$m.

The average number of CA1 neurons/100 $\mu$m of the CA1 cell layer length in the hippocampal sections of the 8 month (FIG. 3B) calcitriol-treated group was about 1.4, while the average number of CA1 neurons/100 $\mu$m in the control group was about 1.2. The calcitonin-treated group of rats had the lowest average number of CA1 neurons/100 $\mu$m with about 1.1 CA1 neurons/100 $\mu$m. These results clearly demonstrate that long term treatment with calcitriol prevents and/or retards neuron loss in aging rats.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for protecting against neuron loss in a subject affected with neuron loss resulting from a neurodegenerative condition, comprising:

(a) providing a compound which protects against neuron loss by acting through a vitamin D receptor; and (b) administering the compound to the subject in an effective amount and over an effective period of time, so as to provide protection against neuron loss.

2. The method of claim 1 wherein the compound is administered over a long term.

3. The method of claim 2 wherein the period of administration is about six months or longer.

4. The method of claim 1 wherein the compound regulates intraneuronal calcium levels.

5. The method of claim 1 wherein the compound regulates peripheral calcium levels.

6. The method of claim 2, wherein the period of administration is about 1 month or longer.

7. The method of claim 1 wherein the compound regulates peripheral phosphate levels.

8. The method of claim 1 wherein the compound regulates intraneuronal phosphate levels.

9. The method of claim 1 wherein the neuron loss is age-related.

10. The method of claim 1 wherein the neuron loss is disease-related.

11. The method of claim 1 wherein the neuron loss is age- and disease-related.

12. The method of claim 1, wherein the neurodegenerative condition is selected from the group consisting of Alzheimer's disease, Pick's disease, Parkinson's disease, Vascular Disease, Stroke, Age Associated Memory Impairment, and Huntington's disease.

13. The method of claim 1 wherein the subject is a mammal.

14. The method of claim 13 wherein the mammal is a human.

15. The method of claim 1 wherein the compound is parenterally administered to the subject.

16. The method of claim 1 wherein the compound is enterally administered to the subject.

17. The method of claim 1 wherein the compound is a biologically active form of vitamin D, a precursor, metabolite, or analog of vitamin D.

18. The method of claim 17 wherein the vitamin D, precursor, metabolite, or analog of vitamin D, is selected from the group consisting of dihydrotachysterol$_2$, dihydrotachysterol$_3$, 5,6-trans-cholecalciferol, 25-hydroxy-5,6-trans cholecalciferol, 1α-hydroxy ergocalciferol, 25-hydroxy ergocalciferol, 1α, 25-dihydroxy ergocalciferol, 1α, 25-dihydroxy cholecalciferol, 1α, 24, 25-trihydroxy cholecalciferol, 24,25-dihydroxy cholecalciferol, 1α, 24-dihydroxy-25-fluoro cholecalciferol, 25-hydroxy cholecalciferol, 1α-hydroxy cholecalciferol, 1α, 25-dihydroxy-B 7-dehydrocholesterol, 1α, 24,25-trihydroxy-7-dehydrocholesterol, 24,25-dihydroxy-7-dehydrocholesterol, 1α-hydroxy-7-dehydrocholesterol, 1α, 24-dihydroxy-25-fluoro-7-dehydrocholesterol, 25,26-dihydroxy-7-dehydrocholesterol, 25-hydroxy-7-dehydrocholesterol, 25-hydroxy ergosterol, 1α, 25-dihydroxy ergosterol, 1α, 25-dihydroxy precholecalciferol, 1α, 24,25-trihydroxy precholecalciferol, 24,25-dihydroxy precholecalciferol, 1α-hydroxy precholecalciferol, 1α, 24-dihydroxy-25-fluoro-precholecalciferol, 25-hydroxy-precholecalciferol, 1α-hydroxy-previtamin D$_2$, 25-hydroxy-previtamin D$_2$, and 1α, 25-dihydroxy-previtamin D$_2$.

19. The method of claim 18 wherein the vitamin D metabolite is calcitriol.

20. The method of claim 1 wherein the compound modulates the biological activity of vitamin D, a precursor, metabolite, or analog of vitamin D, in a manner effective to protect against neuron loss.

21. The method of claim 20 wherein the compound regulates the amount of the vitamin D, precursor, metabolite, or analog of vitamin D, which is available to protect against neuron loss.

22. The method of claim 20 wherein the compound alters the ability of vitamin D, or a precursor or metabolite of vitamin D, to protect against neuron loss.

23. A method according to claim 1, wherein the subject is other than a patient suffering from Alzheimer's disease.

24. A method according to claim 1, wherein the neurodegenerative condition is Alzheimer's disease.

25. A method of protecting against neuron loss in a subject affected with neuron loss resulting from a neurodegenerative condition, comprising:
(a) providing a biologically active form of vitamin D, a precursor, metabolite or analog of vitamin D; and
(b) administering the biologically active form of vitamin D, a precursor, metabolite, or analog of vitamin D to the subject in an amount and over a period of time, determined to be effective to provide protection against neuron loss.

26. The method of claim 25 wherein the subject is a mammal.

27. The method of claim 26 wherein the mammal is a human.

28. The method of claim 25 wherein the vitamin D metabolite is calcitriol.

29. The method of claim 25, wherein the period of administration is about one month or longer.

30. The method of claim 29, wherein the period of administration is about six months or longer.

31. The method of claim 25, wherein the compound is administered over a long term.

32. The method of claim 25, wherein the neurodegenerative condition is selected from the group consisting of Alzheimer's disease, Pick's disease, Parkinson's disease, Vascular Disease, Age Associated Memory Impairment, Stroke, Huntington's disease.

33. A method according to claim 25, wherein the neurodegenerative condition is Alzheimer's disease.

34. A method according to claim 33, wherein the neurodegenerative condition is Alzheimer's disease.

35. A method of protecting against neuron loss in a subject, comprising:
(a) providing a biologically active form of a steroid, or metabolite or analog of a steroid which protects against neuron loss through a mechanism similar to that of vitamin D but not acting through the vitamin D receptor; and
(b) administering the biologically active form to the subject in an amount and over a period of time, determined to be effective without reference to providing acute alleviation of symptoms in the subject, so as to provide protection against neuron loss, such protection being independent of any acute alleviation of such symptoms.

36. A method of protecting against neuron loss in a subject, comprising:
(a) providing a compound other than vitamin D2 or vitamin D3, their corresponding previtamins and provitamins, metabolites and analogues, capable of acting through a vitamin D receptor; and
(b) administering the compound in an amount and over a period of time, determined to be effective so as to provide protection against neuron loss.

37. A method of protecting against neuron loss in a subject at increased risk of neurological impairment by reason of at least one of aging and disease, other than Alzheimer's disease, comprising:
(a) providing a biologically active form of vitamin D, a precursor, metabolite or analog of vitamin D; and (b) administering the biologically active form of vitamin D, a precursor, metabolite, or analog of vitamin D to the subject in an amount and over a period of time, determined to be effective to provide protection against neuron loss.

38. A method of protecting the brain of a subject against neuron loss, comprising:
   (a) providing a compound capable of acting through a vitamin D receptor; and
   (b) administering the compound to the subject in an effective amount and over an effective period of time, so as to provide protection against neuron loss.

39. A method according to claim 38, wherein the subject has an increased risk of neurological impairment by reason of at least one of aging and disease.

40. A method according to claim 39, wherein the subject is suffering from a neurological disease.

41. A method according to claim 40, wherein the subject is suffering from a neurological disease other than Alzheimer's disease.

42. A method for protecting a brain affected with neuron loss resulting from a neurodegenerative condition, comprising:
   (a) providing a compound which protects against neuron loss by acting through a vitamin D receptor; and
   (b) administering the compound to the brain in an effective amount and over an effective period of time, so as to provide protection against neuron loss.

* * * * *

UNITED STATES PATENT AND TRADEMARK OFFICE
CERTIFICATE OF CORRECTION

PATENT NO. : 5,939,407
DATED : August 17, 1999
INVENTOR(S) : Philip W. Landfield It is certified that error appears in the above-identified patent and that said Letters Patent is hereby corrected as shown below:

Please delete Claim 34 as it is duplicative of Claim 33.

Signed and Sealed this

Seventh Day of March, 2000

Attest:

Attesting Officer

Q. TODD DICKINSON
Commissioner of Patents and Trademarks